United States Patent [19]

Chen et al.

[11] 4,229,608
[45] Oct. 21, 1980

[54] HEAT BALANCED CYCLIC PROCESS FOR MANUFACTURE OF LIGHT OLEFINS

[75] Inventors: Nai Y. Chen, Titusville; Werner O. Haag, Lawrenceville, both of N.J.; Rudolph M. Lago, Yardley, Pa.

[73] Assignee: Mobil Oil Corporation, New York, N.Y.

[21] Appl. No.: 970,718

[22] Filed: Dec. 18, 1978

[51] Int. Cl.$^3$ .............................................. C07C 1/00
[52] U.S. Cl. .................................................. 585/640
[58] Field of Search ......................... 260/682; 585/640

[56] References Cited

U.S. PATENT DOCUMENTS

| | | | |
|---|---|---|---|
| 4,046,825 | 9/1977 | Owen et al. | 260/682 |
| 4,062,905 | 12/1977 | Chang et al. | 260/682 |
| 4,134,926 | 1/1979 | Tsao et al. | 260/682 |

*Primary Examiner*—John F. Niebling

*Attorney, Agent, or Firm*—Charles A. Huggett; Michael G. Gilman; Raymond W. Barclay

[57] ABSTRACT

A catalytic heat balanced cyclic process is provided for converting a charge consisting essentially of methanol, dimethyl ether or mixtures thereof to a hydrocarbon product rich in ethylene and propylene by contact, under specified conditions of temperature and contact time, with a catalyst comprising a crystalline aluminosilicate zeolite characterized by pores, the major dimension of which is less than 6 Angstroms and the capability, under such conditions, of producing less than about 20 weight percent methane in said hydrocarbon product, regenerating the catalyst so employed at a temperature between about 1200° and about 1400° F. to remove accumulated carbonaceous deposit therefrom and provide a source of hot regenerated catalyst for further contact, under controlled temperature conditions, with said charge.

10 Claims, 1 Drawing Figure

HEAT BALANCED CYCLIC PROCESS FOR MANUFACTURE OF LIGHT OLEFINS

BACKGROUND OF THE INVENTION

1. Field of the Invention

This invention relates to a continuous heat balanced cyclic process for effecting conversion of methanol, dimethyl ether or mixtures thereof to light olefins utilizing a small pore crystalline aluminosilicate zeolite-containing catalyst.

2. Description of the Prior Art

U.S. Pat. No. 3,036,134 to Mattox discloses conversion of methanol to a reaction product containing water and dimethyl ether in the presence of a sodium or calcium crystalline aluminosilicate zeolite catalyst.

U.S. Pat. No. 3,529,033 to Frilette and Weisz discloses dehydration of a normal alkanol of three to six carbon atoms to an olefin, utilizing a sodium or calcium crystalline aluminosilicate zeolite catalyst having uniform interstitial demensions sufficiently large to admit the alkanol charge and to permit egress therefrom of the olefin product.

U.S. Pat. No. 4,062,905 to Chang et al. discloses a process for selectively converting methanol, dimethyl ether or mixtures thereof to $C_2$—$C_3$ olefins utilizing small pore crystalline aluminosilicate zeolite catalysts.

It has been found, from a practical standpoint, that use of the latter catalysts requires the adoption of certain procedures and necessitates certain precautions such as frequent catalyst regeneration, immediate seperation of the reaction products from the catalyst to eliminate secondary reactions and avoidance of exposure of the catalyst to temperatures above 1400° F. to prevent irreversible deactivation.

SUMMARY OF THE INVENTION

In accordance with the present invention, there is provided a catalytic system for effectively converting methanol, dimethyl ether or mixtures thereof to light olefins in a heat balanced cyclic operation involving a short contact time between the charge and particulate fluidized catalyst and regeneration of the latter under controlled temperature conditions. The process of the instant invention is unique in that it involves heat balancing of two exothermic reactions, since both the reaction zone and the regeneration zone are highly exothermic. This is to be contrasted with more conventional catalytic operations, such as gas oil cracking to gasoline, wherein conversion is effected under endothermic conditions and catalyst regeneration under exothermic conditions and a heat balance maintained between the same.

In brief, the process described herein is directed to a heat balanced cyclic process for converting a charge consisting essentially of methanol, dimethyl ether or mixtures thereof to a hydrocarbon product rich in ethylene and propylene. The process involves contacting the charge with a fluidized catalyst comprising a crystalline aluminosilicate zeolite, characterized by pores, the major dimensions of which are less than 6 Angstroms, further characterized by pore windows of about a size such as would be provided by 8-membered rings of oxygen atoms and the capability, under the condtions of conversion, of producing less than 20 weight percent methane in the resulting hydrocarbon product. Contacting between the specified catalyst, in fluid form, and the charge takes place in a riser reactor at an inlet temperature between about 800° and about 1000° F. with a residence time between catalyst and charge of less than 30 seconds. In the riser-reactor, the temperature increases to within the approximate range of 900° to 1150° F. During such time, a minor proportion of less than about 9 percent by weight of the charge is converted to form a carbonaceous deposit on the catalyst in an amount between about 0.4 and about 1 weight percent. The resulting hydrocarbon product, rich in ethylene and propylene, is thereafter separated from the carbonaceous deposit-containing catalyst. The latter is conducted to a regenerator, maintained at a temperature within the approximate range of 1200° to 1400° F. wherein the carbonaceous deposit is removed from the catalyst by combustion in air. The regenerated catalyst is then recycled to further contact with a fresh stream of the charge and the above cycle repeated.

At the reaction temperature described and under the partial pressure of water, generated as a by-product in the described conversion process, crystalline aluminosilicate zeolite-containing catalysts have heretofore been observed to undergo a very substantial loss in activity by steaming. In contrast to such behavior, the small pore crystalline aluminosilicate catalyst utilized in the present cyclic heat balanced operation of the invention is unexpectedly remarkably stable. Without being limited by any theory, it is postulated that under specified conditions of short contact time and controlled temperature, the hydrocarbon sorbed product and/or the residual carbonaceous deposit, remaining on the catalyst after regeneration, may serve to protect the catalytic sites thereof.

DESCRIPTION OF SPECIFIC EMBODIMENTS

Figure 1:
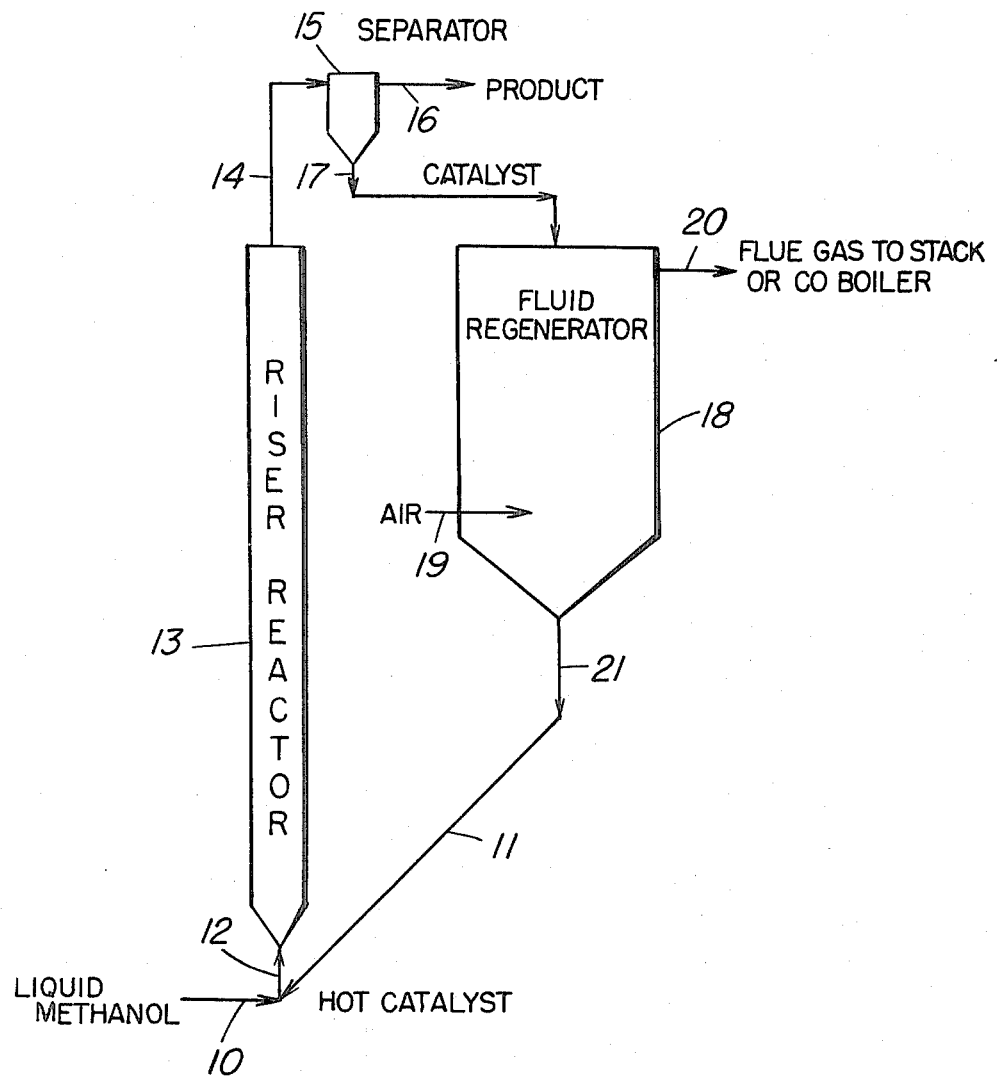
FIG. 1, the single FIGURE of the drawing, depicts a schematic diagram of the heat balanced riser/regenerator system utilized in the process of the invention.

It is contemplated that methyl alcohol, dimethyl ether or mixtures thereof may be used as feed to the process of this invention. The feed may be obtained from any suitable source. For example, methanol feedstock may be manufactured from synthesis gas, i.e. mixture of CO and $H_2$, from coal or may be produced from wood by destructive distillation. Such feed, in accordance with the process described herein, is brought into contact with a stream of small pore crystalline aluminosilicate zeolite catalyst in fluidized form at a temperature between about 1200° and about 1400° F. The weight ratio of catalyst to feed is between about 5 and about 12, with the inlet temperature of the mixture to the reaction zone being between about 800° and about 1000° F. The mixture is conducted to the bottom of a riser reactor where it is subjected to an increased exit temperature of between about 900° and about 1150° F., with a residence time in the riser reactor of less than 30 seconds and preferably less than about 15 seconds. During such time, a major proportion of the feed undergoes conversion to a hydrocarbon product rich in ethylene and propylene and a minor proportion, generally less than about 9 and preferably between about 4 and about 6 percent by weight of the feed is converted to form a carbonaceous deposit on the catalyst amounting to between about 0.4 and about 1 weight percent. The mixture of spent catalyst and hydrocarbon product, rich in ethylene and propylene, is conducted to a separator from which the hydrocarbon gaseous product is withdrawn. If desired, such product may be further separated into its components or group of components by known feasible means. The carbonaceous deposit-containing fluid catalyst is introduced into a regenerator wherein the carbonaceous deposit is burned therefrom, in air at a temperature within the approximate range of 1200° to 1400° F. Flue gas is withdrawn from the regenerator. The regenerated catalyst, at a temperature approximately within the latter range, is recycled to make contact with fresh feed and the above cyclic operation again carried out.

The zeolites utilized herein may be either naturally occurring or synthetic and include, by way of example, erionite, chabazite, zeolite T and zeolite ZK-5. Zeolite T is described in U.S. Pat. No. 2,950,952 and zeolite ZK-5 in U.S. Pat. No. 3,247,195. The crystal structure of the class of zeolites suitable for use as catalysts in the process of this invention is such as to provide access to and egress from the intracrystalline free space of the zeolites by virture of having pores, the major dimension of which is greater than 3 but less than 6 Angstrom units. The zeolites utilized herein are further characterized by pore windows of about a size such as would be provided by 8-membered rings of oxygen atoms. It will be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. The pores characterizing the zeolites useful in the present process may be substantially circular, such as in zeolite ZK-5 having uniform pores of about 3.9 Angstroms or somewhat elliptical, such as in erionite having pores of approximately 3.6 by 5.2 Angstroms. It will be understood that, in any case, the zeolites used as catalysts in the process of this invention have a major pore dimension of less than 6 Angstroms. The pore size dimensions of the above zeolites, as well as other feasible zeolites, are those specified in "Zeolite Frameworks" by W. M. Meier and D. H. Olson appearing in Advances in Chemistry Series, Vol. 101, Pages 155-170 (1971), the contents of which are incorporated herein by reference.

In addition to having the hereinabove described pore size characteristics, the crystalline aluminosilicate zeolite utilized as catalyst in the present process should have the capability of producing a hydrocarbon product containing less than 20 percent and preferably not more than 10 percent by weight of methane. Thus, the calcium form of zeolite A, having pores of approximately 5 Angstroms and commonly referred to as zeolite 5A, while satifying the pore size requirements for zeolites useful as catalysts in the process described herein, is nevertheless, not a particularly feasible catalyst since under the conversion conditions utilized in such process, this zeolite produces considerable amounts of methane, i.e. far in excess of the specified maximum of 20 weight percent characterizing the crystalline aluminosilicate zeolites which have been found to be effective in selectively converting methanol and/or dimethyl ether to ethylene and propylene.

The zeolites useful in the conversion process of this invention generally have at least 10 percent of the cationic sites thereof occupied by ions other than alkali or alkaline earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions, which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

In practicing the desired conversion process, it may be desirable to incorporate the above-described small pore crystalline aluminosilicate zeolites in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or other in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The catalyst is employed in the form of a fluidized mass, the particles of which are of a size between about 40 and about 150 microns. Conversion of the methyl alcohol and/or dimethyl ether charge is carried out in the vapor phase under the conditions specified hereinabove.

The product obtained generally contains steam and a hydrocarbon mixture of paraffins and olefins, substantially devoid of aromatics. The steam and hydrocarbon products may be separated from one another by methods well known in the art. The hydrocarbon product is particularly rich in light olefins, i.e. ethylene and propylene. These compounds usually constitute a major fraction of the total olefin product.

Referring more particularly to FIG. 1, cold liquid methanol introduced through line 10 is mixed with hot regenerated catalyst flowing through line 11 into line 12 at the inlet of the riser reactor 13. The weight ratio of catalyst to methanol so mixed is within the approximate range of 5 to 12. With the temperature of the methanol feed being about 60°–77° F. and that of the hot regenerated catalyst being about 1200°–1400° F., the temperature of the mix entering the riser reactor is generally between about 800° and about 1000° F.

As this gas/solid mixture travels up the riser, the exothermic heat of reaction, amounting to approximately 108–300 cal./gram, corresponding to about 194–540 Btu/lb. of methanol, is dissipated by raising the temperature of the gas/solid mixture by 100° to 200° F. The residence time of the mixture in the riser is less than about 30 seconds and preferably less than about 15 seconds.

The catalyst and conversion products exit from the riser reactor through line 14 and pass into separator 15, where the catalyst is separated from the gaseous products. The latter leave the separator through line 16 and the catalyst through line 17. The separated catalyst generally contains about 0.4 to about 1 weight percent of carbonaceous deposit, which is subsequently removed by combustion in fluid regenerator 18. The regenerator is maintained at approximately 1200°–1400° F., with introduction of air through inlet 19 and withdrawal of flue gas produced through outlet 20. The regenerated catalyst passes from the regenerator through line 21 and is recycled through line 11 to the riser reactor.

To maintain the entire system in thermal balance, approximately 4 to 6 weight percent of the methanol charge is desirably converted to carbonaceous deposit, which is subsequently removed by combustion in the regenerator. In those instances where the carbonaceous deposit is less than the aforenoted amount, the methanol feedstock may be initially preheated before mixing with the hot regenerated catalyst. In those instances where the carbonaceous deposit is more than the aforenoted amount, additional heat removal steps would desirably be employed. Thus, a CO boiler could be attached to the regenerator and the combustion in the regenerator limited to the production of CO from carbonaceous deposit. Another alternative would entail use of a catalyst mixture made up of an active zeolitic component, as above described, mixed with a substantially inert matrix or diluent as silica, clay, alumina or other such refractory inert solid. In this alternative, the concentration of the active component in the catalyst would depend largely on carbonaceous deposit selectivity, i.e. the concentration of zeolite component is adjusted so that the carbonaceous deposit concentration in the solid is between about 0.4 and about 1 weight percent before entering the regenerator to avoid an excessively high temperature therein.

It is to be understood that the foregoing description is merely illustrative of preferred embodiments of the invention of which many variations may be made by those skilled in the art within the scope of the following claims without departing from the spirit thereof.

What is claimed is:

1. A heat balanced cyclic process for converting a charge consisting essentially of methanol, dimethyl ether or mixtures thereof to a hydrocarbon product rich in ethylene and propylene which comprises contacting said charge with a fluidized catalyst comprising a crystalline aluminosilicate zeolite characterized by pores, the major dimension of which is less than 6 Angstroms, further characterized by pore windows of about a size such as would be provided by 8-membered rings of oxygen atoms and the capability, under the hereinafter specified conditions, of producing less than 20 weight percent methane in said hydrocarbon product, said contacting taking place in a riser reactor at an inlet temperature between about 800 and 1000° F. and an increased outlet temperature between about 900° and about 1150° F. with a weight ratio of catalyst to charge between about 5 and about 12 and a residence time between catalyst and charge of less than 30 seconds, during which time, a minor proportion of less than about 9 percent by weight of the charge is converted to form a carbonaceous deposit on said catalyst in an amount of between about 0.4 and about 1 weight percent, thereafter separating the hydrocarbon product, rich in ethylene and propylene from the carbonaceous deposit-containing catalyst, conducting the latter to a regenerator, maintained at a temperature within the approximate range of 1200° to 1400° F., wherein said carbonaceous deposit is removed by combustion in air, recycling the resulting hot regenerated catalyst to further contact with a fresh stream of said charge and repeating the above cycle.

2. The process of claim 1 wherein the charge consists essentially of methanol.

3. The process of claim 1 wherein said residence time is less than about 15 seconds.

4. The process of claim 1 wherein between about 4 and about 6 percent by weight of the charge is converted to form said carbonaceous deposit.

5. The process of claim 1 wherein said crystalline aluminosilicate zeolite is predominantly in the hydrogen form.

6. The process of claim 1 wherein said crystalline aluminosilicate zeolite is contained in a matrix therefor.

7. The process of claim 1 wherein said zeolite is erionite.

8. The process of claim 1 wherein said zeolite is chabazite.

9. The process of claim 1 wherein said zeolite is zeolite T.

10. The process of claim 1 wherein said zeolite is zeolite ZK-5.

* * * * *